United States Patent [19]

Saito et al.

[11] Patent Number: 4,843,173

[45] Date of Patent: Jun. 27, 1989

[54] PROCESS FOR PRODUCING GLUCONIC ACID

[75] Inventors: Hisashi Saito, Murayama; Shinji Ohnaka; Shigeo Fukuda, both of Kawagoe, all of Japan

[73] Assignees: Kawaken Fine Chemicals Co., Ltd.; Kao Corporation, both of Tokyo, Japan

[21] Appl. No.: 195,466

[22] Filed: May 16, 1988

Related U.S. Application Data

[63] Continuation of Ser. No. 888,097, Jul. 17, 1986, abandoned, which is a continuation of Ser. No. 662,937, Oct. 19, 1984, abandoned.

[30] Foreign Application Priority Data

Oct. 24, 1983 [JP] Japan ................................ 58-198872

[51] Int. Cl.$^4$ .............................................. C07C 51/16

[52] U.S. Cl. .................................................... 562/531
[58] Field of Search ......................................... 562/531

[56] References Cited

U.S. PATENT DOCUMENTS

| | | | |
|---|---|---|---|
| 3,607,922 | 9/1971 | Acres et al. | 562/531 |
| 3,655,747 | 4/1972 | Sennewald et al. | 562/531 |
| 4,108,891 | 8/1978 | Hattori et al. | 562/531 |
| 4,620,034 | 10/1986 | Smits | 562/531 |

*Primary Examiner*—Paul J. Killos
*Attorney, Agent, or Firm*—Flynn, Thiel, Boutell & Tanis

[57] ABSTRACT

Gluconic acid is produced by oxidizing glucose with an oxygen-containing gas in an aqueous alkali solution in the presence of a palladium-bismuth/carbon catalyst which has adsorbed firstly bismuth and secondly palladium. The catalyst has an improved activity, selectivity and durability.

5 Claims, 1 Drawing Sheet

X-RAY PATTERN OF 5% PD-10% BI-CARBON OBTAINED IN EXAMPLE 2

X-RAY PATTERN OF 5% PD-5% BI-CARBON OBTAINED IN EXAMPLE 1

X-RAY PATTERN OF THE CATALYST OBTAINED IN COMPARATIVE EXAMPLE 2

PROCESS FOR PRODUCING GLUCONIC ACID

This application is a continuation of U.S. Ser. No. 888,097, filed July 17, 1986, which is a continuation of U.S. Ser. No. 662,937, filed Oct. 19, 1984, both now abandoned.

The present invention relates to a process for producing gluconic acid by oxidizing glucose in the presence of a catalyst. More particularly, the invention relates to a process for producing gluconic acid by oxidizing glucose with an oxygen-containing gas in an aqueous alkali solution in the presence of a catalyst containing bismuth and palladium.

Oxidized monosaccharides are used in various industrial fields. The most typical examples of them are gluconic acid and its salts. They are used widely as a chelating agent, detergent for the surface of a metal such as iron or aluminum and also for the glass surface, builder for detergents, concrete admixture, medicines and food additives. The present invention will be described with reference to gluconic acid.

Gluconic acid is now produced mainly by a fermentation process on an industrial scale. This process is the easiest and economically most excellent process. However, it has many defects such as difficulties in the separation of microbes, control of by-products and disposal of waste water.

To overcome the defects of the fermentation process, there have been proposed catalytic oxidation processes wherein gluconic acid is produced by reacting glucose with molecular oxygen in the presence of a noble metal catalyst such as platinum or palladium under an alkaline condition as disclosed, for example, in the specification of Japanese Patent Publication No. 7620/1958.

However, the process disclosed in the above-mentioned specification wherein 2% palladium/carbon catalyst is used in an amount of as large as about 10 wt. % based on glucose requires a reaction time of 5 to 8 h and the yield is as low as 80 to 85%. When glucose is oxidized at a reaction temperature of 50° to 55° C. at pH 10, the resulting product is colored in deep red and has a very poor quality.

The inventors previously proposed a process for oxidizing monosaccharides as disclosed in the specification of Japanese Patent Publication No. 37333/1978. Though it was described therein that the yield of sodium gluconate obtained by this process was at least 97%, the following fact has been elucidated by further investigations: since the yield was determined according to a gas chromatographic analysis of trimethylsilylated sodium gluconate, the peak of said gluconate and those of silylated saccharic acid and mannose as byproducts overlap each other and, therefore, the yield thus determined was higher than the real yield. In the subsequent investigations, the inventors determined sodium gluconate enzymatically by using an enzyme reagent which reacts selectively with sodium gluconate to reveal that the yield of sodium gluconate obtained by the process disclosed in the above-mentioned specification was 85 to 90%.

A palladium-bismuth catalyst is disclosed in the specification of Japanese Patent Laid-Open No. 163340/1982 which relates to a process for producing 2-keto-L-gulonic acid. In this process, a hydroxyl group of L-sorbose (ketose) is oxidized with oxygen in the presence of a catalyst containing palladium and bismuth to obtain 2-keto-L-gulonic acid in a yield of 85%. The process of the present invention is characterized in that not the hydroxyl group but an aldehydo group of glucose (aldose) is oxidized to obtain gluconic acid. The process of the present invention is different from the above-mentioned process in the functional group to be oxidized and the intended product. It has been unknown in the prior art that the palladium-bismuth catalyst selectively oxidizes only the aldehydo group of glucose as an aldose, leaving the hydroxyl group non-oxidized.

Other reasons why the catalytic oxidation process is not employed for the production of gluconic acid on an industrial scale are as follows: as compared with the fermentation process for the production of gluconic acid, the catalytic oxidation process has the following defects: (a) unreacted glucose remains in a large amount, (b) gluconic acid having a low purity is obtained in a poor yield and (c) a high purity is required of starting glucose.

More particularly, glucose is isomerized into fructose in the oxidation reaction in an aqueous alkali solution. As the glucose conversion is increased, the oxidation proceeds excessively to form saccharic acid in addition to intended gluconic acid and also other side reactions proceed to reduce the purity and yield of gluconic acid. Further, when commercial glucose is used as the starting material, it is difficult to obtain gluconic acid in a high yield, since impurities contained therein exert influences on the catalyst to make the reacton impossible or to lower the reaction rate seriously. Thus, the gluconic acid production costs of the conventional catalytic oxidation processes have been far higher than those of the fermentation processes.

Under these circumstances, the development of a process for producing gluconic acid with a high production efficiency and free from the above-mentioned defects by using a catalyst having an excellent activity, selectivity and durability has been demanded.

After intensive investigations on the production of gluconic acid made for the above-mentioned purpose, the inventors have found that when a palladium-bismuth/carbon catalyst prepared by a specified process is used, glucose can be oxidized with a high selectivity to form gluconic acid in a high yield. The present invention has been completed on the basis of this finding. The present invention provides a process for producing gluconic acid by oxidizing glucose with an oxygen-containing gas in an aqueous alkali solution, characterized by using a palladium-bismuth/carbon catalyst prepared by allowing an active carbon containing a previously adsorbed bismuth compound to support a palladium compound thereon and reducing the same.

The present invention will now be described in detail. The previously proposed processes for producing the palladium-bismuth catalyst are ineffective for the oxidation of glucose. The oxidation activity varies remarkably according to the order of adsorbing bismuth and palladium on the active carbon. Namely, only the palladium-bismuth/carbon catalyst of the present invention prepared by allowing an active carbon containing a previously adsorbed bismuth compound to support a palladium compound thereon exhibits high activity and selectivity in the oxidation of glucose.

Reasons for this phenomenon have not been elucidated yet. According to an X-ray diffraction of the catalyst of the present invention, a diffraction pattern due to an alloy composition of palladium and bismuth is observed. However, no diffraction pattern due to the allow composition is obtained when a commercially available palladium/carbon catalyst is treated with a bismuth compound. It is supported, therefore, that the catalyst having the palladium-bismuth alloy composition is capable of carrying out the reaction quantatively without leaving unreacted reactants and without forming by-products.

BRIEF DESCRIPTION OF DRAWINGS

FIGS. 1 and 2 show the X-ray diffraction patterns of two catalysts according to the invention. FIG. 1 shows the X ray diffraction of the catalyst consisting of 5 wt.% of palladium and 10 wt.% of bismuth on carbon. FIG. 2 shows that of the catalyst consisting of 5 wt.% of palladium and 5 wt.% of bismuth on carbon. Both show a peak corresponding to the alloy composition of palladium and bismuth. On the other hand, FIG. 3 shows that of the catalyst which falls outside of the scope of the invention, obtained by treating a conventional catalyst of 5 wt.% of palladium on carbon with a bismuth salt, but it does not have the peak of the alloy composition of palladium and bismuth.

Figure 1:
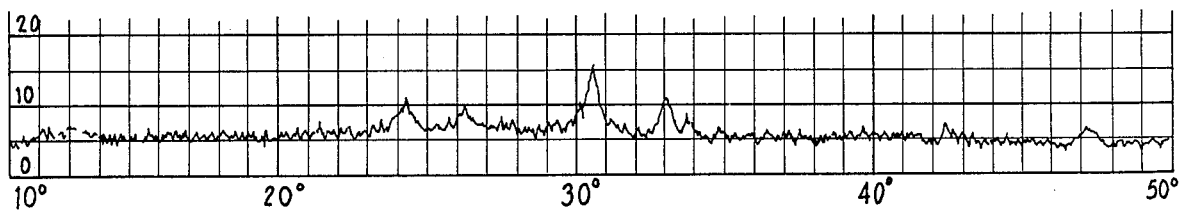
FIGS. 1 and 2 are X ray diffraction patterns of catalysts according to the invention.

The present invention will now be illustrated with reference to an embodiment thereof.

The catalyst used in the present invention is prepared as follows. Active carbon is suspended in water and an aqueous solution of a bismuth compound dissolved by using hydrochloric acid is added to the suspension. The mixture is stirred to effect adsorption of the bismuth compound by the active carbon. An aqueous palladium chloride solution is added to the suspension to allow palladium chloride to be adsorbed completely by the active carbon treated with the bismuth compound (alternatively, the active carbon treated with bismuth is dried at 100 to 200° C. and then palladium chloride is adsorbed thereon). The palladium and bismuth compounds are reduced with formalin or formic acid. After filtration, the filter cake is washed with water to obtain a palladium-bismuth/carbon catalyst. The catalyst is used for the oxidation reaction as it is or after drying. An X-ray diffraction pattern of this catalyst indicates that it is an alloy of bismuth and palladium.

The catalyst is added to a 5 to 50% aqueous glucose solution and then oxygen or an oxygen-containing gas is blown therein. Simultaneously, an aqueous solution of an alkali such as sodium hydroxide is added dropwise to the reaction mixture under stirring at a temperature maintained at 30° to 60° C. As the reaction proceeds, gluconic acid is formed. An alkali is added dropwise thereto so as to neutralize the acid. The amount of the alkali to be added is controlled so that the pH of the solution will be in the range of 8 to 11, preferably 9 to 10. The progress of the reaction can be recognized by the amount of the alkali consumed. When glucose has been exhausted, no more alkali is consumed and the reaction no more proceeds. Thus, the reaction proceeds rapidly and quantitatively. After completion of the reaction, the catalyst is filtered to obtain a colorless or slightly yellow aqueous alkali gluconate solution. For many industrial purposes, the catalyst filtered out of the reaction product may be used as it is or after concentration or crystallization thereof by an ordinary method. Another advantage of the invention is that gluconic acid and glucono-δ-lactone can be produced easily by an ion exchange method.

The most preferable catalyst carrier used in the present invention is active carbon, though alumina, silica/alumina and diatomaceous earth may also be used. The active carbon in fine powder is capable of attaining a higher reaction rate and, therefore, it inhibits the isomerization and increases the yield.

The metal compounds which can be used for the prepartion of the catalyst of the present invention include bismuth compounds such as bismuth trichloride, bismuth trioxide, bismuth oxychloride and bismuth hydroxide nitrate and palladium compounds such as palladium chloride, palladium nitrate, palladium oxide and palladium hydroxide. These metals or compounds are sparingly soluble in water and, therefore, they should be dissolved in a mineral acid such as hydrochloric acid or aqua regia before being adsorbed by the active carbon. As for the order of the adsorption of these metals by the active carbon, it is necessary that the bismuth compound be first adsorbed by the active carbon and then the palladium compound be adsorbed thereon.

The amounts of bismuth and palladium metals to be adsorbed by the active carbon are not particularly limited. However, the amounts are preferably not exceeding saturation adsorption of the heavy metals on the active carbon. The palladium-bismuth/carbon catalyst carrying 0.01 to 20 wt. % of bismuth and 1 to 10 wt. % of palladium is preferably prepared.

The catalyst according to the process of the present invention is used in such an amount that the reaction can be completed at a low pH in a short time, since glucose is easily isomerized in the aqueous alkali solution to reduce the yield of gluconic acid. For example, at least 0.5 wt. %, preferably 1 to 2 wt. %, based on glucose, of 5% palladium-5% bismuth/carbon catalyst is used.

In the process of the present invention, the pH value lowers as the reaction proceeds. Therefore, an alkali such as an aqueous sodium hydroxide solution is added to the reaction mixture as required to maintain the pH in the range of 8 to 11, preferably 9 to 10.

The oxygen-containing gas used as the oxidizing agent in the process of the present invention include oxygen and air.

In the process of the present invention, the reaction is effected at 20° to 100° C., preferably 30° to 60° C., under atmospheric pressure or preferably elevated pressure of up to about 10 atm. The reaction rate, etc. can be improved by carrying out the reaction under the elevated pressure.

As compared with the conventional processes, the process of the present invention has the following merits.

(1) Extremely high activity and selectivity are obtained in the oxidation reaction of glucose. More particularly, glucose is oxidized quantitatively within a short time, unreacted substances are left in only a very small amount, side reactions are controlled and gluconic acid is obtained in a high yield.

(2) The amount of the catalyst required is small and the catalyst can be used repeatedly many times.

(3) The reaction time is as short as 1 to 4 h, while that required in the fermentation process is at least 12 h.

(4) Starting glucose having a quality over a wide range can be used to obtain gluconic acid at a low cost.

(5) Gluconic acid having a high purity which requires no purification in the production of glucono-δ-lactone can be obtained.

The following examples will further illustrate the present invention.

EXAMPLE 1

[Preparation of the catalyst]

Figure 2:
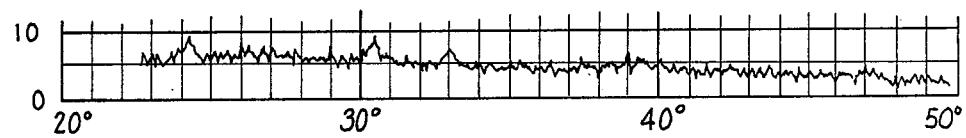

8.4 g (5 g in terms of bismuth) of bismuth hydroxide nitrate was dissolved in 50 m; of concentrated hydrochloric acid. Water was added to the solution to make the total volume 1 l. 90 g of a commercially available active carbon was added thereto and the mixture was stirred at room temperature for 6 to effect the adsorption. 33.4 g (5 g in terms of palladium) of a palladium chloride solution containing 15 wt. % of palladium metal was added dropwise to the suspension under stirring to allow the palladium salt to be completely adsorbed by the active carbon. The suspension was made alkaline by adding 200 g of a 20 wt. % aqueous sodium hydroxide solution thereto. 24 ml of formalin was added to the suspension and the mixture was maintained at a temperature of 80±5° C. for 1 h to reduce the bismuth and palladium salts. After filtration followed by washing with water and drying, 5% palladium-5% bismuth/carbon catalyst was obtained. This obtained catalyst was analyzed with the X ray diffractometry. The result is shown in FIG. 2.

[Oxidation of glucose]

1200 g of an aqueous solution of 360 g (2 mol) of glucose (HI MESH; a product of Aito Co., Ltd.) and 5.4 g (1.5 wt. % based on glucose) of the catalyst prepared as above were placed in a 2.5 l reaction vessel provided with a stirrer, thermometer, alkali dropping funnel, pH electrodes and oxygen inlet. Oxygen gas was introduced into the aqueous solution under vigorous stirring while the temperature was maintained at 50±1° C. As the reaction proceeded, gluconic acid was formed. Gluconic acid was neutralized with a 40 wt. % aqueous sodium hydroxide solution added dropwise thereto so as to maintain the pH of the aqueous solution at 9.5±0.2. 1.0 h after the initiation of the reaction, a theoretical amount (2 mol) of the alkali was consumed. Thereafter, no more alkali was consumed and the reaction no more proceeded. Thus, the completion of the reaction was evident.

The catalyst was filtered out of the reaction mixture to obtain a colorless, transparent filtrate. A part of the filtrate was analyzed according to high performance liquid chromatography to determine unreacted glucose and isomerized sugar (fructose). Sodium gluconate was determined by an enzymatic analysis (enzyme reagent; a product of Boehringer Mannheim GmbH). The results were as follows:

Glucose conversion: 99.8%
Sodium gluconate selectivity: 99.7%
Yield of sodium gluconate: 99.5%
Rate of isomerization into fructose: 0.1%

EXAMPLE 2

Catalysts were prepared in the same manner as in Example 1 except that the bismuth content was varied and then glucose was oxidized under the same conditions as in Example 1. The results are shown in Table 1. Among them, the catalyst of 5% of palladium and 10% of bismuth on carbon was found to have an X ray pattern shown in FIG. 1.

TABLE 1

| Amount of bismuth (based on active carbon (%) | Reaction time (h) | Glucose Conversion (%) | Sodium gluconate Selectivity (%) | Yield (%) |
|---|---|---|---|---|
| 0 | 1.0 | 93.8 | 90.3 | 84.7 |
| 0.1 | 1.0 | 99.5 | 96.5 | 96.0 |
| 1.0 | 1.0 | 99.8 | 98.9 | 98.7 |
| 2.5 | 1.0 | 99.8 | 98.2 | 98.0 |
| 5.0 | 1.0 | 99.8 | 99.7 | 99.5 |
| 10.0 | 1.0 | 99.8 | 99.7 | 99.5 |

EXAMPLE 3

5% palladium-2.5% bismuth/carbon catalyst was obtained in the same manner as in Example 1 except that bismuth hydroxide nitrate was replaced with 2.8 g (2.5 g in terms of bismuth) of bismuth oxide.

Glucose was oxidized in the presence of 5.4 g of this catalyst in the same manner as in Example 1. One hour was required for completion of the reaction. The glucose conversion was 99.9% and the yield of sodium gluconate was 98.0%.

EXAMPLE 4

Tests were effected by using 5.4 g of the same catalyst as in Example 1 repeatedly. In the tests, glucose was oxidized in the same manner as in Example 1 and, after completion of the reaction, the catalyst was filtered from the reaction product and used as it was in the reaction in the next batch. This procedure was repeated to obtain the results shown in Table 2.

TABLE 2

| Number of times of repetition | Reaction time | Yield of sodium gluconate (%) |
|---|---|---|
| 1 | 1.0 h | 99.5 |
| 2 | 1.0 | 99.8 |
| 3 | 1.2 | 97.8 |
| 4 | 1.2 | 99.5 |
| 5 | 1.4 | 99.5 |
| 6 | 1.5 | 97.4 |
| 7 | 1.7 | 96.4 |
| 8 | 1.7 | 97.2 |
| 9 | 2.0 | 97.4 |
| 10 | 2.0 | 96.7 |

COMPARATIVE EXAMPLE 1

A 5% palladium/carbon catalyst was prepared without treatment of the active carbon with the bismuth salt. More particularly, 95 g of a commercially available active carbon was suspended in 1 l of water. 33.4 g of a palladium chloride solution containing 15 wt. % (in terms of metallic palladium) of palladium chloride was added dropwise to the suspension to allow the palladium salt to be completely adsorbed by the active carbon. 75 g of a 20 wt. % aqueous sodium hydroxide solution was added thereto to make the suspension alkaline. 12 ml of formalin was added to the suspension and the mixture was maintained at 80±5° C. for 1 h. After a filtration followed by washing with water and drying, a 5% palladium/carbon catalyst was obtained.

Glucose was oxidized in the presence of 5.4 g of the catalyst in the same manner as in Example 1. It took 1.0 h to complete the reaction. The glucose conversion was 93.8% and the yield of sodium gluconate was 84.7%. According to a high performance liquid chromatographic analysis, the formation of saccharic acid was recognized.

COMPARATIVE EXAMPLE 2

Figure 3:
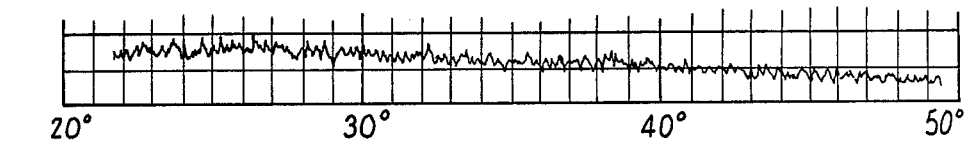
FIG. 3 is an X-ray diffraction pattern of the prior catalyst.

1.7 g (1 g in terms of bismuth) of bismuth hydroxide nitrate was dissolved in 10 ml of concentrated hydrochloric acid. Water was added to the solution to make the total volume 200 ml. 20 g of the 5% palladium/carbon catalyst obtained in Comparative Example 1 was added to the solution and the mixture was stirred at room temperature for 1 h. The mixture was made alkaline with an aqueous sodium hydroxide solution. 2.4 ml of formalin was added thereto and the mixture was maintained at 80±5° C. for 1 h. After filtration of the catalyst followed by washing with water and drying, a palladium-bismuth catalyst was obtained. This obtained catalyst was analyzed by the X ray diffractiometry with a result shown in FIG. 3.

Glucose was oxidized in the presence of 5.4 g of this catalyst in the same manner as in Example 1. The reaction rate was low. One hour after th initiation of the reaction, the alkali consumption was only 25% based on the theoretical amount. It was thus confirmed that the catalyst obtained by after-treatment of the palladium/carbon catalyst with the bismuth compound can not exhibit its effects in the oxidation of glucose.

The embodiments of the invention in which an exclusive property or privilege is claimed are defined as follows:

1. A process for producing gluconic acid, which comprises:
    contacting an aqueous alkaline reaction solution containing a glucose with an oxygen-containing gas, while simultaneously adding an alkali at a rate effective to maintain the pH of said reaction solution in the range of 8 to 11, in the presence of a catalyst which comprises palladium and bismuth supported on a carbon carrier whereby to convert said glucose into a salt of gluconic acid, said catalyst is prepared by adsorbing a bismuth compound on active carbon carrier, then adsorbing a palladium compound on said active carbon carrier containing adsorbed bismuth compound and then reducing said bismuth compound and said palladium compound to obtain said catalyst.

2. A process as claimed in claim 1, in which said active carbon consists of fine particles.

3. A process as claimed in claim 1, in which said bismuth compound is selected from the group consisting of bismuth trichloride, bismuth trioxide, bismuth oxychloride and bismuth hydroxide nitrate and said palladium compound is selected from the group consisting of palladium chloride, palladium nitrate, palladium oxide and palladium hydroxide.

4. A process as claimed in claim 1, in which said catalyst contains 0.01 to 20 percent by weight of bismuth and 1 to 10 percent by weight of palladium.

5. A process for producing gluconic acid, which comprises:
    blowing an oxygen-containing gas into an aqueous reaction solution containing from 5 to 50 wt. % of glucose, having a temperature of 30° to 60° C. and containing a catalytically effective amount of a catalyst consisting essentially of an alloy composition of palladium and bismuth supported on a carbon carrier, and simultaneously adding an aqueous solution of an alkali at a rate effective to maintain the pH of said reaction solution in the range of 8 to 11 whereby to prepare an alkali gluconate;
    said catalyst containing from 0.01 to 20 wt. % of bismuth, from 1 to 10 wt. % of palladium and the balance is essentially carbon, said catalyst is prepared by adsorbing a bismuth compound on active carbon carrier, then adsorbing a palladium compound on said active carbon carrier containing adsorbed bismuth compound and then reducing said bismuth compound and said palladium compound to obtain said catalyst.

* * * * *